United States Patent [19]
Kock et al.

[11] Patent Number: 5,678,540
[45] Date of Patent: Oct. 21, 1997

[54] BREATHING GAS SYSTEM

[75] Inventors: Mikael Kock, Akersberga; Claes Eng, Jaerfaella, both of Sweden

[73] Assignee: Siemens Elema AB, Solna, Sweden

[21] Appl. No.: 408,836

[22] Filed: Mar. 23, 1995

[30] Foreign Application Priority Data

Mar. 24, 1994 [SE] Sweden .................. 9400992

[51] Int. Cl.$^6$ .................................. A62B 9/00
[52] U.S. Cl. .................. 128/205.13; 128/205.14; 128/205.15; 128/205.17
[58] Field of Search .............. 128/205.13, 205.14, 128/205.15, 205.17, 205.23

[56] References Cited

U.S. PATENT DOCUMENTS

| | | | |
|---|---|---|---|
| 3,831,595 | 8/1974 | Valenta et al. | 128/205.15 |
| 5,299,579 | 4/1994 | Gedeon et al. | 128/205.15 |
| 5,398,675 | 3/1995 | Henkin et al. | 128/205.15 |
| 5,490,499 | 2/1996 | Heinonen et al. | 128/205.15 |

FOREIGN PATENT DOCUMENTS 433 722   3/1986   Sweden .

OTHER PUBLICATIONS

Servo Anesthesia Circle 985, Operating Manual, pp. 1:6–1:7, Jul. 1991.

Primary Examiner—Aaron J. Lewis
Attorney, Agent, or Firm—Hill, Steadman & Simpson

[57] ABSTRACT

A breathing gas system, primarily intended for use during anaesthetization of patients, has a respiratory circuit, a drive gas apparatus and a pressure-transmitting bellows device, connected by a first space to the respiratory circuit and by a second space to the drive gas apparatus. When an outlet valve is regulated at the end of an expiratory phase to minimize the pressure difference between the first space and the second space, the respiratory circuit responds immediately at the next inspiratory phase when drive gas is sent to the second space. Minimizing the pressure difference also makes possible use of the pressure-regulated operating mode with the breathing gas system, and a rapid response to attempts at spontaneous breathing by the patient is achieved.

7 Claims, 1 Drawing Sheet

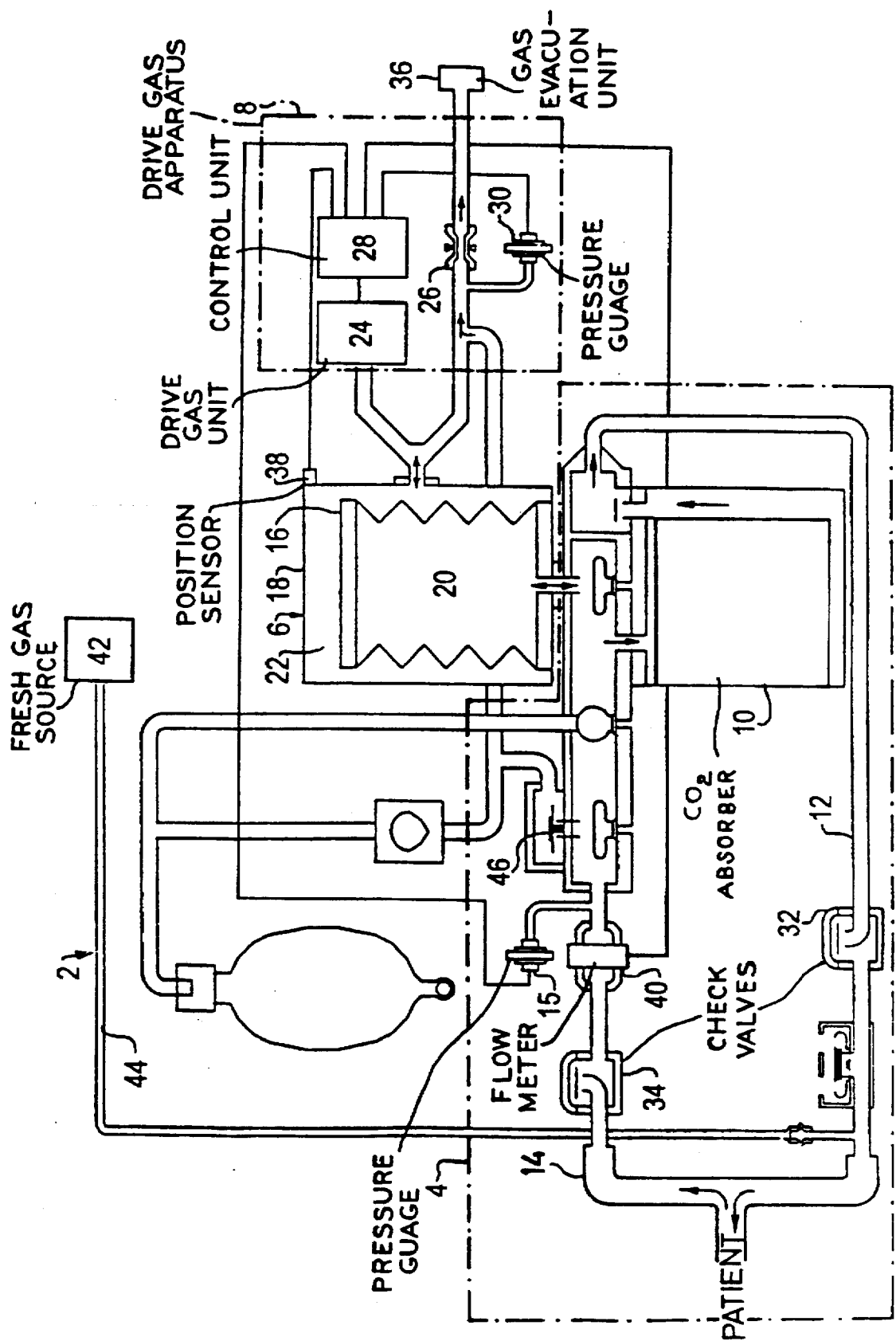

BREATHING GAS SYSTEM

BACKGROUND OF THE INVENTION

1. Field of the Invention

The present invention is directed to a breathing gas system, and specifically to an anaesthesia system.

2. Description of the Prior Art

Breathing gas systems are known of the general type having a respiratory circuit for carrying a breathing gas to and from a patient, a pressure gauge for measuring pressure in the respiratory circuit, a drive gas apparatus for controlling the flow of breathing gas in the respiratory circuit and a pressure-transmitting unit. In such known systems, the pressure-transmitting unit has a first space connected to the respiratory circuit, a second space connected to the drive gas apparatus and a movable body which separates the first space from the second space so the volume of the first space increases when the volume of the second space decreases and vice-versa, whereby pressure changes can be transmitted between the drive gas apparatus and the respiratory circuit.

One such known breathing gas system is described in Swedish Published Application 443 722. This breathing gas system is an anaesthesia system having a respiratory circuit for connection to a patient, a bag-and-bottle device and a drive unit for controlling the flow of breathing gas in the respiratory circuit. The bag-and-bottle device has a bellows arranged in a container, with the interior of the bellows is connected to the respiratory circuit, and the space between the bellows and the walls of the container is connected to the drive unit. When an inspiratory phase is to commence, the drive unit supplies a drive gas to the space between the bellows and the container. As the pressure in this space exceeds the pressure in the bellows, the bellows is compressed, and breathing gas be conducted to the patient. An expiratory phase follows the inspiratory phase. During the expiratory phase, breathing gas is discharged from the space between the bellows and the container. This causes the development of a relative overpressure in the respiratory circuit and bellows. The bellows therefore expands, and breathing gas can flow out of the patient's lungs. This is repeated in each respiratory cycle.

For this type of anaesthesia system, the anaesthetist normally presets the tidal volume, i.e. the volume of breathing gas the patient is to receive in each breath. In the above described known anaesthesia system, this is accomplished by limiting the bellows mobility inside the container between two end positions. When the bellows is compressed during inspiration, a volume corresponding to the bellows volume between the two end position!5 is conveyed to the patients lungs. When preset in this manner, the tidal volume cannot easily be changed after the patient has been attached to the anaesthesia system. This makes major demands on the anesthesiologist and his or her staff to ensure that a suitable setting is made for each patient, since there is no alarm system for erroneous tidal volumes. In addition, both the inspirator 37 phase and the expiratory phase must be long enough to give the bellows time to assume both end positions.

Another disadvantage of this known anaesthesia system is that the patient is not allowed to breathe spontaneously. Instead, every breath is forced on the patient. Especially when the patient is losing or regaining consciousness, she or he generally strives to breathe spontaneously. Forced inspirations which are not synchronized with spontaneous breaths can be very uncomfortable to the patient.

The aforementioned problems have been solved in part in another known anaesthesia system, the Servo Anaesthesia Circle 985, which is described in an Operating Manual, pp. 1:6–1:7, Siemens-Elema AB, July 1991. This anaesthesia system also has a respiratory circuit, a pressure-transmitting bellows device and a drive system. Regulation of the tidal volume, however, differs completely from the aforementioned anaesthesia system. Instead of limiting the bellows movement, the Servo Anaesthesia Circle 985 is devised to control the tidal volume by regulating the flow of drive gas to the space between the bellows and the container. Drive gas is then sent to the space for a preset inspiration duration. The flow and inspiration duration determines the tidal volume which is forced on the patient.

With this known system, the patient can also trigger an inspiratory phase when attempting to breath spontaneously.

This known system, however, has not solved all of the aforementioned problems. For both described known anaesthesia system, the space between the bellows and the container must at the onset of the inspiratory phase first be filled with enough drive gas to raise the pressure in the space to the pressure which is present in the bellows. Until that stage is reached, the bellows cannot be compressed. There will therefore be a delay before actual inspiration commences. This is the case irrespective of whether the inspiratory phase is mandatory or triggered by the patient's attempts to inhale.

Since the drive gas is only added for a preset inspiratory duration in the latter prior art anaesthesia system, the tidal volume can vary and, in the worst instance, be less than the desired tidal volume.

SUMMARY OF THE INVENTION

An object of the present invention is to achieve a breathing gas system according to the general type described above which solves the remaining problems.

Such a breathing gas system is achieved in accordance with the invention wherein the breathing gas system has an additional pressure gauge for measuring pressure in the second space and a control device, connected to the pressure gauge and the additional pressure gauge, for controlling the drive gas apparatus on the basis of the gas pressures measured so that the pressure difference between the second space and the respiratory circuit is minimized after the conclusion of expiration.

Regulation of the pressure difference during the final stage of the expiratory phase means that the second space does not have to be filled with drive gas at the onset of the following inspiratory phase in order for breathing gas to be forced toward the patient. An immediate response is therefore achieved in the flow of breathing gas to the patient when new drive gas is supplied to the second space. This also produces a number of other advantages. In known breathing gas systems of this general type, i.e., with a pressure-transmitting unit, only a few operating modes are possible. In principle, only volume control and volume support, in which a preset tidal volume of breathing gas is delivered to the patient, are possible. In addition to these operating modes, a number of other modes are known in connection with ventilators/respirators which operate without a pressure-transmitting unit. Two of these other known operation modes are pressure control and pressure support. These latter operating modes have thus not been available with the known anaesthesia systems (or with any breathing: system utilizing a pressure-transmitting unit). The breathing gas system according to the present invention, however, operates better than the known systems and can therefore be used for all known operating modes in the entire ventilator/respirator art. This is because the pressure difference between the respiratory circuit and the second space in the pressure-transmitting unit is regulated in the described manner.

One advantageous way of minimizing the pressure difference after expiration is achieved in accordance with the invention in an embodiment wherein the drive gas apparatus has an adjustable outlet valve through which gas can be bled from the second space, and the control device controls the outlet valve at the final phase of expiration to equalize pressure between the second space and the respiratory circuit.

A refinement of the invention is achieved by making the respiratory circuit a closed gas flow circle for rebreathing of the breathing gas.

There are a number of known principles for respiratory circuits in conjunction with anaesthesia system. The most economical respiratory circuit is the rebreathing circle. In the rebreathing circle most of the breathing gas exhaled by the patient is immediately reused at the following inspiration. Carbon dioxide is removed by filtration, and a certain amount of fresh gas is added from a gas source to compensate for the intake of oxygen and anaesthetic in the patient's body.

In this context, it is advantageous to incorporate a pressure relief valve in the respiratory circuit for releasing gas from the respiratory circuit at an adjustable maximum patient pressure.

In anaesthesia, for example, an overpressure of 3 cm $H_2O$ in the respiratory circuit is normally acceptable. If the pressure rises above this level, the pressure relief valve will open and release the surplus gas. For some patients another maximum overpressure is more suitable.

It is also advantageous for the movable body, as in the known devices to consist of a bellows arranged inside a cylindrical container, whereby the interior of the bellows forms the first space, and the space between the bellows and the container forms the second space.

A further improvement of the breathing gas system is achieved in accordance with the invention in an embodiment employing a level sensor arranged at the container for emitting a sensor signal when the bellows is at a predetermined distance from its most expanded position.

In this way, regulation of the outlet valve can be arranged so the valve is completely open at the onset of the expiratory phase so as to facilitate expiration to the greatest possible extent. When the bellows approaches its end position at the end of the expiratory phase, the sensor sends a signal to the control device which immediately starts regulating the outlet valve to minimize the pressure difference between the first space and the second space.

It is an advantage to incorporate an efficient triggering function for spontaneous breathing into the breathing gas system. The respiratory circuit has an inspiratory line and an expiratory line. Triggering can thus be accomplished by placing the pressure gauge in the expiratory line, and placing a flow meter in the expiratory line which is connected to the control device in order to measure a flow of gas in the expiratory line. The control device, on the basis of measurement values from the pressure gauge, the additional pressure gauge and the flow meter, determines whether the patient is attempting an inspiration and then controls the drive gas apparatus so an inspiratory phase commences.

DESCRIPTION OF THE DRAWINGS

The single FIGURE illustrates one embodiment of a breathing gas system according to the invention.

DESCRIPTION OF THE PREFERRED EMBODIMENTS

The breathing gas system 2 includes a respiratory circuit 4, a pressure-transmitting bellows device 6 and a drive gas apparatus 8. The respiratory circuit 4 includes, in turn, a $CO_2$ absorber 10 for removing carbon dioxide from the breathing gas, an inspiratory line 12 for carrying breathing gas to a patient and an expiratory line 14 for carrying gas away from the patient. A first pressure gauge 15, is arranged in the expiratory line 14 to measure the pressure in the respiratory circuit 4.

The pressure-transmitting bellows device 6 has a bellows 16 arranged inside a container 18 so a first space 20, connected to the respiratory circuit 4, is formed inside the bellows, and a second space 22, connected to the drive gas apparatus 8, is formed between the bellows 16 and the container 18. Pressure is transmitted between the first space 20 and the second space 22 when the bellows 16 expands and collapses inside the container 18. Since the first space 20 is connected to the respiratory circuit 4, the first pressure gauge 15 also indirectly measures the pressure in the first space 20.

The drive gas apparatus 8 includes a drive gas unit 24, which supplies drive gas to the second space 22, an outlet valve 26 through which drive gas is evacuated from the second space 22, a control device 28 which controls both the drive gas unit 24 and the outlet valve 26 and a second pressure gauge 30 for measuring the pressure in the drive gas apparatus 8 and, accordingly, indirectly measuring the pressure in the second space 22.

The pressure gauges 15 and 30 are connected to the control device 28 which among other things regulates the outlet valve 26 on the basis of the pressure difference between the first space 20 and the second space 22.

The breathing gas system 2 operates according to the following principle. When an inspiration is to be imposed on the patient, the control device 28 closes the outlet valve 26 completely and regulates the drive gas unit 24 in such a way that a predetermined flow of drive gas is conveyed to the second space 22 for a predetermined inspiration duration. The bellows 16, starting from its most expanded position, will then be compressed, and breathing gas will flow out of the first space 20.

In the respiratory circuit 4, the direction of breathing gas flow is controlled by a first check (one-way) valve 32, arranged in the inspiratory line 12, and a second check valve 34, arranged in the expiratory line 14. The breathing gas will therefore flow through the $CO_2$ absorber 10 into the inspiratory line 12 to the patient.

When, at the end of the inspiratory phase, the drive gas unit 24 stops supplying drive gas to the second space 22, pressure equilibrium develops between the first space 20 and the second space 22. The bellows 16 has then been compressed so much that a specific tidal volume (according to the predetermined flow of drive gas and inspiration duration) has been forced out and into the respiratory circuit 4 and into the patient's lungs. As soon as the pressure equilibrium has developed, breathing gas will stop flowing through the inspiratory line 12.

In principle, control of the breathing gas system 2 can be performed so the state of equilibrium is retained for a brief period of time, i.e. an inspiratory pause.

Irrespective of whether an inspiratory pause is used, the expiratory phase starts with the opening by the control device 28 of the outlet valve 26. The out-let valve 26 is appropriately opened completely to facilitate expiration. The drive gas in the second space 22 will then begin to flow out through the outlet valve 26 to a gas evacuation unit 36.

The pressure drop in the second space 22 causes the bellows 16 to begin expanding, since there is now a relative overpressure in the respiratory circuit 4 and the first space 20. The breathing gas supplied to the patient can now begin to flow out and into the expiratory line 14 through the second check valve 34 and fill the bellows 16.

A position sensor 38, arranged at the container 18, senses when the bellows 16 begins to approach its most expanded position at the end of the expiratory phase. The position sensor 38 is connected to the control device 28. The control device 28 starts regulating the outlet valve 26 when the position sensor 38 emits a signal indicating that the bellows 16 is approaching its end position. Regulation of the outlet valve 26 is on the basis of the pressures measured by the pressure gauges 15 and 30 and aims at minimizing the pressure difference between the first space 20 and the second space 22. The same pressure thus can prevail in both spaces 20 and 22 as early as at the end of the expiratory phase.

When the pressure difference between the first space 20 and the second space 22 is minimal, breathing gas is delivered to the patient as soon as drive gas is again supplied to the second space 22 in the next inspiratory phase. This is because the slightest overpressure in the second space 22 causes the bellows 16 to begin collapsing, thereby expressing breathing gas. In other words, the respiratory circuit 4 responds immediately when drive gas is supplied or evacuated from the second space 22.

This is a major difference compared to known breathing gas systems in which the second space must first be filled with gas to the same pressure prevailing in the first space before the respiratory circuit starts responding.

Minimizing the pressure gradient also produces advantages other than a rapid response in mandatory inspiration. In the ventilation of a patient without a pressure-transmitting bellows device 6, for example, treatment modes can be employed which were heretofore not available when a pressure-transmitting bellows device 6 is arranged in the system, e.g. the pressure control mode or the pressure support mode. In the pressure control operating mode, the patient's lungs are subjected to a mandatory, preset breathing gas pressure throughout the entire inspiratory phase. In the pressure support mode, (another) preset breathing gas pressure is delivered to the patient each time she or he triggers an inspiratory phase. This could be an appropriate mode for patients who are regaining consciousness after anaesthesia.

As a result of minimization of the pressure difference between the first space 20 and the second space 22 in the final part of the expiratory phase, the breathing gas system 2 according to the invention can operate in any known mode, since the respiratory circuit 4 responds so rapidly to the drive gas apparatus 8. In particular, the breathing gas system 2 according to the present invention can operate according to any of the known modes in the ventilator/respirator art. In addition to the aforementioned operating modes, the breathing gas system 2 is especially suitable for the volume control mode, the volume support mode and the pressure regulated volume control mode (PRVC).

The breathing gas system 2 is therefore also designed for use in supporting patients who try to breathe spontaneously. An attempt at inspiration by the patient will then trigger an inspiratory phase by the drive gas apparatus 8. In order to identify an attempt at inspiration, the control device 28 is connected to a flow meter 40 arranged in the expiratory line 14. During expiration, a flow of gas passes the flow meter 40. When the patient attempts an inspiration, the second check valve 34 blocks the flow of gas in the expiratory line 14, and the flow meter 40 then senses the absence of any gas flow. The flow meter 40 supports a signal to the control unit 28, which causes an inspiration can then be activated. If fresh gas is continuously supplied, as described below, the flow meter 40 will sense a decline in the flow of gas through the expiratory line 14 when the patient attempts an inspiration. The control device 28 can also utilize the pressures measured by the pressure gauges 15 and 30 for making a more reliable assessment of whether the patient is attempting inspiration.

Since the patient consumes oxygen and, in some instances, anaesthetic gas, replenishment of fresh gas in the respiratory circuit 4 becomes necessary. This is supplied by a source of fresh gas 42 which, via a fresh gas line 44, sends fresh gas to the inspiratory line 12. To prevent the buildup of excessive positive pressure in the respiratory circuit 4, a pressure relief valve 46 is arranged in the expiratory line 14. The pressure relief valve 46 is devised to open at an adjustable overpressure in relation to atmospheric pressure, preferably at an overpressure of 3 cm $H_2O$, and discharge surplus gas through the outlet valve 26. The discharge of surplus gas occurs mainly during the expiratory phase. Gas can also be discharged to a separate evacuation unit, but only one evacuation unit is needed for all gas, thereby facilitating minimization of the pressure difference.

In this embodiment, the respiratory circuit 4 has been depicted with a rebreathing circle in which the breathing gas is immediately reused after removal of carbon dioxide from the breathing gas. The respiratory circuit 4 can alternatively employ some other known respiratory circle utilizing a pressure-transmitting bellows device, e.g., the Bain system which has no $CO_2$ absorber but instead employs a larger flow of fresh gas to prevent excessive rebreathing of carbon dioxide.

The drive gas apparatus 8 can consist of an integrated apparatus or can be formed by several connected units.

Although modifications and changes may be suggested by those skilled in the art, it is the intention of the inventors to embody within the patent warranted hereon all changes and modifications as reasonably and properly come within the scope of their contribution to the art.

We claim as our invention:

1. A breathing gas system comprising:
    a respiratory circuit for carrying a breathing gas to and from a patient, executing a series of inspirations and expirations in successive respiratory cycles;
    first pressure gauge means for measuring pressure in said respiratory circuit;
    drive gas means for controlling a flow of breathing gas in said respiratory circuit;
    pressure-transmitting means including a first space, having a volume, connected to said respiratory circuit, a second space having a volume, connected to said drive gas means, and a movable body separating said first space from said second space so that the volume of said first space increases when the volume of the second space decreases and vice-versa, for transmitting pressure changes between said drive gas means and said respiratory circuit;
    second pressure gauge means for measuring a pressure in said second space; and
    control means, connected to said first and second pressure gauge means, for controlling said drive gas means dependent on the respective pressures measured by said first and second pressure gauge means for minimizing a pressure difference between said second space and said respiratory circuit after each expiration by a patient.

2. A breathing gas system as claimed in claim 1 wherein said drive gas means includes adjustable outlet valve means for bleeding gas from said second space, and wherein said control means comprises means for controlling said outlet valve at a final phase of expiration for equalizing pressure between said second space and said respiratory circuit.

3. A breathing gas system as claimed in claim 1 wherein said respiratory circuit comprises a closed gas flow circuit for rebreathing of gas respirated by a patient.

4. A breathing gas system as claimed in claim 3 further comprising:

a fresh gas source connected to said respiratory circuit for supplying fresh breathing gas to said respiratory circuit; and pressure relief valve means connected in said respiratory circuit for discharging gas from said respiratory circuit when said gas in said respiratory circuit reaches a selected maximum pressure.

5. A breathing gas system as claimed in claim 1 wherein said pressure-transmitting means comprises:

a cylindrical container; and a bellows disposed inside said cylindrical container, said bellows having an interior forming said first space and said bellows and said container having a space therebetween forming said second space.

6. A breathing gas system as claimed in claim 5 wherein said bellows, as said volume of said first space increases, reaches a most expanded position, and said breathing gas system further comprising position sensor means disposed in said container for emitting a sensor signal when a top of said bellows is at a predetermined distance from said most expanded position.

7. A breathing gas system as claimed in claim 1 wherein said respiratory circuit includes an inspiratory line and an expiratory line, wherein said second pressure gauge means is disposed in said expiratory line, and said breathing gas system further comprising flow meter means connected in said expiratory line for measuring a flow of gas in said expiratory line and for emitting a signal corresponding to said flow of gas in said expiratory line to said control means, and said control means comprising means, dependent on pressure measured by said second pressure gauge means and flow measured by said flow meter means, identifying when a patient is attempting an inspiration and for controlling said drive gas means for commencing an inspiratory phase.

* * * * *